(12) United States Patent
Zimmer et al.

(10) Patent No.: US 7,523,680 B2
(45) Date of Patent: Apr. 28, 2009

(54) GAS MEMBRANE SAMPLING DEVICE AND GAS SENSOR DEVICE FOR GEOLOGICAL INVESTIGATIONS

(75) Inventors: Martin Zimmer, Schwielowsee-Caputh (DE); Jörg Erzinger, Schwielowsee-Caputh (DE)

(73) Assignee: Helmholtz-Zentrum Potsdam Deutsches GeoForschungsZentrum-GFZ, Potsdam (DE)

( * ) Notice: Subject to any disclaimer, the term of this patent is extended or adjusted under 35 U.S.C. 154(b) by 273 days.

(21) Appl. No.: 11/434,345

(22) Filed: May 15, 2006

(65) Prior Publication Data

US 2007/0261503 A1     Nov. 15, 2007

(51) Int. Cl.
*G01N 1/00*     (2006.01)
(52) U.S. Cl. .................................... 73/863.23
(58) Field of Classification Search .............. None
See application file for complete search history.

(56) References Cited

U.S. PATENT DOCUMENTS

| | | | |
|---|---|---|---|
| 3,871,228 A | | 3/1975 | Weiss |
| 4,550,590 A | | 11/1985 | Kesson |
| 5,010,776 A | * | 4/1991 | Lucero et al. ............ 73/863.23 |
| 5,235,863 A | * | 8/1993 | Bailey et al. ............. 73/863.23 |
| 5,333,609 A | | 8/1994 | Bedingham et al. |
| 5,902,939 A | * | 5/1999 | Ballard et al. ............ 73/863.12 |
| 6,487,920 B1 | * | 12/2002 | Robbat, Jr. ............... 73/863.12 |
| 6,679,096 B1 | | 1/2004 | Lazik et al. |
| 7,434,446 B2 | * | 10/2008 | Johnson et al. ............. 73/19.1 |
| 2004/0089079 A1 | * | 5/2004 | Engebretson ............ 73/863.23 |
| 2004/0154414 A1 | * | 8/2004 | LaCourse et al. ......... 73/863.23 |

FOREIGN PATENT DOCUMENTS

EP     0429397 B1     1/1998

OTHER PUBLICATIONS

Lazik, D. et al; "A new method for membrane-based gas measurements", Sensors and Actuators A, vol. 117 (2005) pp. 241-251.

Watson, J. et al.; "Gas Monitoring instrument utilising fibre optic, piezoelectric and gas-sensitive polymer techniques", Sensors and Actuators B, vol. 34 (1996) pp. 323-327.

Nanto, H. et al; "A smart gas sensor using polymer-film-coated quartz resonator microbalance", Sensors and Actuators B, vol. 66 (2000) pp. 16-18.

Straková, Mária et al; "Silicone membrane measuring system with SnO$_2$ gas sensor for on-line monitoring of volatile organic compounds in water", Sensors and Actuators B, vol. 52 (1998) pp. 274-282.

Zee, Frank et al; "Micromachined polymer-based chemical gas sensor array", Sensors and Actuators B, vol. 72 (2001) pp. 120-128.

Kesson, J.; "The diffusion of gases through a silicone rubber membrane, and its application to an in-line carbonation meter", MBAA Technical Quarterly, vol. 21, No. 3, 1984, pp. 143-146.

* cited by examiner

*Primary Examiner*—Robert R Raevis
(74) *Attorney, Agent, or Firm*—Drinker Biddle & Reath LLP

(57) ABSTRACT

A gas membrane sampling device, particularly for geological investigations, comprises a membrane element including a liquid-tight, gas-permeable membrane, a filler material contained in and stabilizing the membrane element, and a connection cable being adapted for conducting gas out of the membrane element through a bore hole to a surface of the earth's. A gas sensor device for geological investigations, comprises the gas membrane sampling device and an analyzing device connected with the connection cable of the gas membrane sampling device. Furthermore, a method for the investigation of a geological formation is described.

22 Claims, 1 Drawing Sheet

GAS MEMBRANE SAMPLING DEVICE AND GAS SENSOR DEVICE FOR GEOLOGICAL INVESTIGATIONS

FIELD OF THE INVENTION

The invention is related to the field of gas analysis in deep geological formations, in particular to a gas membrane sampling device and to a gas sensor device, as well as to methods of using these devices.

RELATED PRIOR ART

The continuous investigation and direct determination of the gas composition of subsurface brines in deep boreholes is an indispensable tool for the characterization of existing natural fluids and the monitoring of changes of reservoir gases during industrial use. The conventional techniques used for this purpose comprise e.g. fluid production with submersible pumps, lift tests and down hole fluid samplers. These techniques provide the only possibility for the execution of direct measurements and for obtaining uncontaminated gases from a deep reservoir horizon for detailed geochemical and isotopes studies. However, the conventional methods have essential disadvantages as they represent expensive and sophisticated techniques.

Furthermore, the application of phase separating membranes is generally known in applied sciences, medicine and industry for gas analysis purposes. With this technique, membranes are used as a gas-permeable phase boundary, that can be passed by gases only. As an example, a membrane is arranged at a boundary between water and gas. Gas resolved in the water can pass the membrane for a specific analysis on the membrane's gas side. Conventional membrane systems have been used e.g. in environmental gas analysis with laboratory gas chromatographs, membrane-based catheters for in vivo-analysis of blood gas composition, membrane-based measurements for process control in food industry (e.g. adjustment of $CO_2$ concentration during beverage manufacturer), and in solid-state gas sensors having encapsulated gas-permeable membrane films. The application of a conventional membrane-based techniques is restricted to compact apparatuses allowing an immediate analysis of the gas passed through the membrane. These apparatuses can be used in a laboratory or otherwise protected environment only. Furthermore, the application of the membrane-based techniques was restricted to typical measurement conditions with atmospheric pressure and room temperature.

OBJECTIVE OF THE INVENTION

The objective of the invention is to provide improved devices and methods being suitable for subsurface gas measurements, in particular in geological formations, and avoiding the disadvantages of the conventional geological measurement techniques. In particular, the devices of the invention should have an improved structure in terms of easy handling, avoiding complex mechanical components and reducing costs. Furthermore, there is an interest in providing a technique allowing to obtain gases from deep reservoir horizons for detailed geochemical and isotopes studies.

SUMMARY OF THE INVENTION

According to a first aspect of the invention, the above objective is solved by a gas membrane sampling device, particularly for geological investigations, having a membrane element including a liquid-tight, gas-permeable membrane, which can be used as a gas-permeable phase boundary, wherein the gas membrane sampling device further comprises a gas-permeable filler material arranged in an inner space of the membrane element and a connection cable connecting the inner space of the membrane element with an outer surface outside of a geological formation under investigation, in particular with the earth's surface.

The combination of a phase-separating membrane element with the inner filler material and the connection cable advantageously allows a continuous collection of gas in the geological formation and a continuous conveyance of the collected gas to the surface. The connection cable permits the conduction of the subsurface gas phase into an analytical device at the surface so that a real-time gas analysis and/or possibly further gas collection is provided at the surface. Advantageously, the restrictions of conventional techniques, in particular with regard to the discontinuous operation and complexity of the structure are avoided.

Contrary to the conventional membrane-based gas analysis systems, the gas membrane sampling device of the invention can be used as a gas collector under extreme conditions in a borehole. The inventors have found that the operation principle of the conventional membrane-based gas analysis can be used for collecting and analysis gases in geological investigations. For the first time, a phase separating membrane, like e.g. a silicon membrane, which is permeable for gases to be investigated, is used for extracting the gases dissolved in borehole fluids, water or brines.

According to the invention, the membrane element is mechanically stabilized with the gas-permeable filler material. Advantageously, the filler material provides the inner space in the membrane element even with high pressure conditions present in a borehole in the geological formation. Preferably, the filler material comprises particles, in particular spheres of a solid inert material, filling the inner space in the membrane element. Solid particles provide a gas-permeable solid package allowing a migration of the sample gas to the connection cable. Particularly preferred is the use of glass or ceramic spheres as filler material, which have been found to exhibit a sufficient hardness for withstanding the high pressures in boreholes. Alternatively or additionally, the filler material comprises an inert gas, like e. g. Ar, provided under pressure in the membrane element.

According to a further preferred embodiment of the invention, the gas membrane sampling device comprises a membrane casing forming a container accommodating the membrane element. Advantageously, the membrane casing provides a mechanical protection of the membrane element against unintended mechanical forces possibly occurring in the borehole. If the membrane casing includes a metal tube, further advantages are obtained in terms of an adaptation to the inner shape of the borehole. The membrane casing may have an open free end for allowing a liquid in the borehole to contact the membrane element. According to a particularly preferred embodiment of the invention, the membrane casing and in particular the metal tube comprises a wall perforation so that the direct contact of the liquid phase in the geological formation with the membrane element is improved.

According to a particularly preferred embodiment of the invention, an adapter device is arranged in the membrane element for coupling the connection cable to the membrane element. The adapter device preferably includes two capillary adapter elements for connecting capillaries included in the connection cable with the membrane element. Advantageously, the adapter device allows a simple combination and if necessary separation of the connection cable and the membrane element.

According to a further modification of the invention, a filter device is arranged between the adapter device and the connection cable. Advantageously, the filter device fulfills a cleaning function such that gaseous materials can enter the connection cable only, while solid materials are retained with the filter device. In particular, the filler material contained in the membrane element is retained by the filter device. Accordingly, an unintended introduction of the filler material into the connection cable is avoided.

The gas-conducting capillaries included in the connection cable are preferably made of stainless steel, which fulfills a sealing function. Using stainless steel capillaries along the whole length from the membrane element to the surface (about 1000 m or more, e. g. up to 4 km), an unintended introduction of foreign gases or gas leakage are avoided. Accordingly, the sensitivity and reproducibility of the gas analysis can be improved.

Advantageously, the connection cable used according to the invention can fulfill a double function. Additionally to the gas conduction, the connection cable can include at least one electrically conducting element, which allows a transmission of electrical signals from optional sensors, like e.g. pressure sensors or temperature sensors. Preferably, at least one sensor is included in the membrane element. Alternatively, the sensor can be arranged adjacent to the membrane element in the membrane casing or even in the borehole. For obtaining an improved signal transmission, the connection cable preferably includes at least one, preferably two double core wires. Alternatively or additionally, at least one of the gas-conducting capillaries can be used as an electrically conducting element.

According to a further particularly preferred embodiment of the invention, the membrane element comprises a silicon membrane. The inventors have found that surprisingly conventional silicon membrane can be used with the gas sampling device of the invention. It has been found that the silicon membranes are stable enough to withstand the extreme pressure, e. g. up to 150 bar or even higher and temperature conditions in the borehole. Furthermore, silicon membranes have a special advantage in terms of a high gas permeation rate, in particular $CO_2$ permeation rate.

According to a second independent aspect of the invention, the above objective is solved by a gas sensor device for geological investigations, comprising the gas membrane sampling device according to the invention and an analyzing device connected with the connection cable of the gas membrane sampling device. The gas sensor device of the invention has the particular advantage that, at the surface, the gas phase can be analyzed directly and/or it can be sampled for a more detailed investigation in a laboratory. Advantageously, any type of analysis principle can be used for operating the analyzing device. The gas sensor device is compatible with conventional analyzing equipment. According to particular preferred embodiments of the invention, the analyzing device preferably includes at least one of a mass spectrometer, an electro-chemical gas sensor and a gas chromatography device.

According to further alternatives of the invention, the analyzing device includes at least one of a radiation detector and a gas sample collecting device. The radiation detector is adapted for sensing ionizing radiation. It comprises e.g. an α-scintillator. The gas sample collecting device is adapted for taking at least one sample of the collected gas for a more detailed investigation in a laboratory. Preferably, the gas sample collecting device is arranged for an automatic collection of a plurality of different samples. For this purpose, the gas sample collecting device can be operated in dependence on a control signal derived from the analyzing device, in particular from the mass spectrometer or other sensors.

According to a particularly preferred embodiment of the invention, the gas sensor device comprises a carrier gas source, which is connected with the connection cable of the gas membrane sampling device, in particular with one of the capillaries included in the connection cable. Preferably, the carrier gas source is a pressure gas source including a pressure vessel. With the carrier gas source, a carrier gas can be introduced via the connection cable to the membrane element. The carrier gas stream introduced into the membrane element is loaded with the gas to be investigated and conducted with the second capillary in the connection cable back to the surface. The pressure gas source is capable to urge the carrier gas stream with an increased pressure into the membrane element so that a flowing carrier gas stream can be facilitated even under high-pressure conditions in the borehole. Furthermore, the pressure gas source is used to provide an inner gas pressure in the membrane element stabilizing the membrane against the outer borehole pressure.

Preferably, the carrier gas source contains an inert gas selected in dependence on the particular application. As examples, noble gases, like Ar or Xe, or pure $N_2$ can be used as an inert gas.

According to a third independent aspect of the invention, the above objective is solved by a method for the investigation of a geological formation, wherein the gas membrane sampling device according to the invention is used for carrying gas from the geological formation to the earth's surface and the gas is analyzed and/or collected at the surface with an analyzing device. The gas carried through the connection cable to the surface comprises a carrier gas and at least one gas to be investigated, which is sampled with the gas membrane sampling device. The analysis is conducted directly at the end of the connection cable with the analyzing device. Alternatively, the carried gas is collected with the gas sample collection device being a part of the analyzing device and moved to another location, e.g. a laboratory for further analysis.

According to a particular advantageous application of the invention, the gas to be investigated includes carbon dioxide. There is a particular interest in investigating this gas in geological formations. Furthermore, extended experiences in measuring carbon dioxide exist in conventional membrane-based gas analyzing systems.

BRIEF DESCRIPTION OF THE DRAWINGS

Further details and advantages of the invention are explained in the following description with reference to the attached drawings. The drawings show in.

PREFERRED EMBODIMENTS OF THE INVENTION

The invention is described as follows in an exemplary manner with reference to an embodiment where the gas membrane sampling device is provided with a silicon elastomer membrane. It is emphasized that the implementation of the invention is not limited to this configuration but is an alternative to that extent that other membrane materials can be used, which are known from conventional membrane-based gas sensing. It is furthermore emphasized that the illustrations shown here are not scale drawings. The absolute sizes and size relationships and conditions can be selected depending on the concrete application requirements when implementing the invention.

Figure 1:
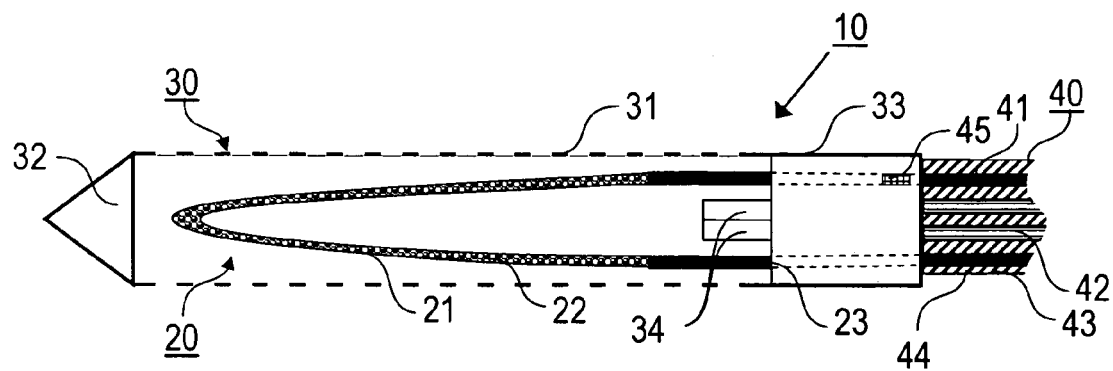
FIG. 1: a schematic cross-sectional view of a preferred embodiment of the gas membrane sampling device according to the invention.

The embodiment of a gas membrane sampling device 10 according to the invention, as shown in FIG. 1 in schematic cross-sectional view, comprises the membrane element 20, the membrane casing 30, the filter device 45 and the connection cable 40.

The membrane element 20 comprises a cylinder-shaped or tubular membrane 21, which is spanning an inner space filled with the filler 22. The ends of the membrane 21 are connected with two capillary adapters 23. The membrane 21 comprises a silicon elastomer membrane tube with a thickness in the range of 0.5 mm to 1.5 mm. The diameter and length of the membrane element 20 are about 6 mm and 50 cm, respectively. For improving the sensitivity, the length of the membrane element 20 can be increased up to 1 m to 2 m or even larger. The filler 22 comprises glass spheres with a diameter of e.g. 0.1 mm to 0.2 mm. The glass spheres prevent the membrane from collapsing and permit to keep its form and allow a carrier gas, like e.g. Argon to pass through.

The capillary adapters 23 provide transition elements for connecting the capillaries (see below) of the connection cable 40 to the membrane element 20. Each capillary adapter 23 comprises a tube with an opening at a free distal end and a screw-connector at the proximal end directed to the connection cable 40. Each capillary adapter 23 has a cone shape for allowing a smooth transition from the material of the membrane 21 to the solid adapter material, like e.g. a stainless steel.

The membrane casing 30 comprises a perforated tube-shaped metal housing 31 made of e.g. Al. The diameter and the axial length of the membrane casing 30 are e. g. 6 cm and 1 m, resp. A free end of the housing has a closing wall, preferably with the shape of a housing tip 32. At the opposite end, the housing 31 is provided with a connecting socket 33. The membrane element 20 is loosely accommodated in the membrane casing 30. Furthermore, sensors 34 are arranged in the membrane casing 30, like e. g. a temperature and a pressure sensor. According to an alternative embodiment, the membrane element may comprises a balloon-shaped membrane including the filler material, which balloon-shaped membrane is fixed to the connecting socket. In this case, the capillary adapters are arranged in the balloon-shaped membrane.

The connection cable 40 includes an inflow capillary 41, an outflow capillary 44 and optionally at least one electrically conducting element 42, which are embedded in a strain relief element 43. The capillaries 41, 44 comprise stainless steel capillaries ($1/16$"). Two electrically conducting elements 42 are provided as a double core wire transmitting electrical signals from the sensors 34 of the gas sampling device 10.

The gas sampling with the gas sampling device 10 is based on the following physical model, which essentially is known from conventional membrane-based gas sensing. The physics of the gas transfer from a liquid environment into the dry inner space of the membrane element 20 is described with a solution-diffusion model based on the assumption of adsorption and desorption of the gas on the membrane surface and dissolution and diffusion of the gas through the material of the membrane 21. The permeation of the gas through the membrane 21 proceeds in several steps. At first gas is adsorbed from the liquid environment at the outer surface of the membrane 21. Once the gas molecule is adsorbed, desorption or adsorption will occur depending on the energetics of the surface. Gas molecules are considered as being dissolved into the membrane phase. Inside the membrane, the gas molecules diffuse according to the concentration gradient along the radial direction (along the membrane thickness). If the gas molecules reach the inner membrane surface, the mass transfer proceeds in reverse order, i.e. gas leaves the membrane phase and is subsequently desorbed into the inner space. In the inner space of the membrane element 20, the flowing carrier gas introduced through the inflow capillary 41 is loaded with the desorbed gas. The gas mixture is led through the second capillary 44 to the surface of the borehole.

Figure 2:
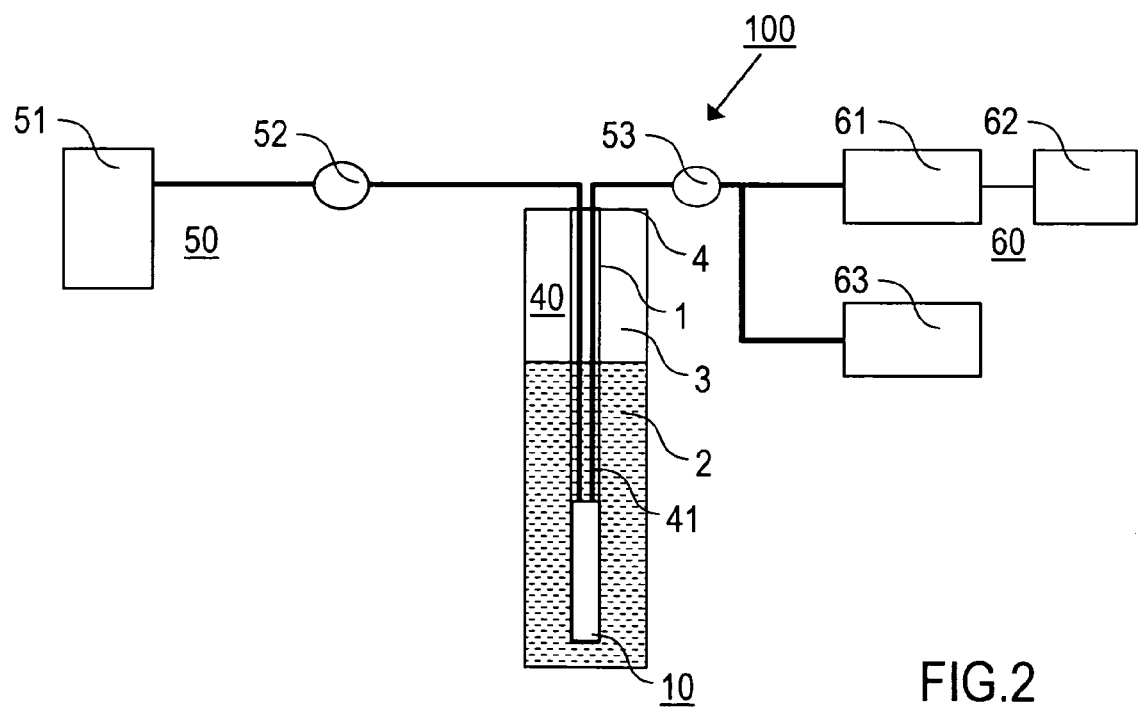
FIG. 2: a schematic view of a preferred embodiment of the gas sensor device according to the invention.

A preferred embodiment of a gas sensor device 100 according to the invention including the above gas membrane sampling device 10 is schematically illustrated in FIG. 2. A borehole 1 has been formed in the earth' crust including a plurality of geological formation 2, 3 below the earth surface 4. The borehole 1 has a depth of e.g. 1 km. The outer pressure around the gas membrane sampling device 10 is about 100 bar. Due to the filler 21 contained in the membrane element 20 and the additional prevailing Ar pressure, collapsing of the membrane element 20 is avoided.

According to FIG. 2, the gas sensor device 100 comprises the carrier gas source 50, the analyzing device 60 and the gas sample collecting device 70. Both components 60 and 70 are connected with the outflow capillary 44 of the connection cable 40.

The carrier gas source 50 is connected with the inflow capillary 41 of the connection cable 40. Device 50 comprises a pressure vessel 51 including pressurized Argon, a first gas flow control unit 52 for adjustment of the gas flow into the gas membrane sampling device 10 and a second gas flow control unit 53, e. g. a needle valve, for adjustment of the gas pressure in the membrane element 20. The gas flow control units 52, 53 are operated such that the pressure in the membrane element 20 of the device 10 is about e. g. 1 . . . 100 bar or even higher.

The analyzing device 60 comprises a quadrupole mass spectrometer 61, a data acquisition unit 62 and a gas sample collecting device 63. The spectrometer 61 is adapted for sensing e.g. $H_2$, He, $CH_4$, $N_2$, $O_2$, Ar and $CO_2$. The data acquisition unit 62 is operated as it is known from conventional mass spectrometer device. Through considering the permeation rates of different gases through the membrane and the Henry-constants on gas solubility, the gas concentration dissolved in the water surrounding the membrane element can be calculated.

The gas sample collecting device 63 comprises a plurality of reservoir vessels for collecting samples of the carrier gas (Argon) loaded with the gas to be investigated. As an example, eight reservoir vessels are provided each having an electromagnetic valve, which can be operated in dependence on a trigger signal. The trigger signal can be obtained from the mass spectrometer 61 for filling different samples into different reservoirs. The reservoirs of the gas sample collecting device 63 can be separated from the gas membrane sampling device 10 for further analysis in a laboratory.

The gas sensor device 100 is operated according to the following procedure. Using pressurized Argon a constant Argon stream is applied via the inflow capillary 41 to the membrane element 20 (see FIG. 1). The dissolved borehole gases being in contact with a membrane element 20 permeate through the membrane 21 and will be transported together with the Argon stream via the outflow capillary 44 to the surface 4. Here, the gas phase will be analyzed with the quadrupole mass spectrometer 61 and/or gas samples will be collected for further laboratory investigations.

The features of the invention disclosed in the above description, the drawings and the claims can be of significance both individually as well as in combination for the realization of the invention it its various embodiments.

What is claimed is:

1. Gas membrane sampling device for geological investigations, comprising:
    a membrane element comprising a cylinder-shaped or tubular gas-permeable membrane that is liquid-tight relative to a liquid environment of the membrane element,
    a filler material comprising spheres of a solid inert material, said filler material contained within an inner space of the membrane element and stabilizing the membrane element, and
    a connection cable being adapted for conducting gas out of the inner space of the membrane element through a bore hole to a surface location.

2. The gas membrane sampling device according to claim 1, wherein the solid inert material comprises glass or ceramic spheres.

3. The gas membrane sampling device according to claim 1, further comprising a membrane casing forming a container accommodating the membrane element.

4. The gas membrane sampling device according to claim 3, wherein the membrane casing comprises a metal tube.

5. The gas membrane sampling device according to claim 4, wherein the metal tube has a perforation.

6. The gas membrane sampling device according to claim 1, wherein the membrane element comprises two capillary adapter elements for connecting the connection cable with the membrane element.

7. The gas membrane sampling device according to claim 6, wherein a filter device is arranged between the capillary adapter elements and the connection cable.

8. The gas membrane sampling device according to claim 1, wherein the connection cable includes two capillaries for introducing or withdrawing a carrier gas to or from the membrane element.

9. The gas membrane sampling device according to claim 8, wherein the capillaries include stainless steel capillaries.

10. The gas membrane sampling device according to claim 1, wherein the connection cable includes at least one electrically conducting element.

11. The gas membrane sampling device according to claim 10, wherein the electrically conducting element comprises at least one double core wire.

12. The gas membrane sampling device according to claim 1, wherein the membrane element comprises a silicone membrane.

13. A gas sensor device for geological investigations, comprising:
    a gas membrane sampling device, the gas membrane sampling device comprising
        a cylinder-shaped or tubular membrane element comprising a gas-permeable membrane that is liquid-tight relative to a liquid environment of the membrane element,
        a filler material comprising spheres of a solid inert material, said filler material contained within an inner space of the membrane element and stabilizing the membrane element, and
        a connection cable being adapted for conducting gas out of the inner space of the membrane element through a bore hole to a surface location, and
    an analyzing device connected to the connection cable.

14. The gas sensor device according to claim 13, wherein the analyzing device includes at least one of a mass spectrometer, an electro-chemical gas sensor and a gas chromatography device.

15. The gas sensor device according to claim 13, wherein the analyzing device includes at least one of a radiation detector for sensing ionizing radiation and a gas sample collecting device.

16. The gas sensor device according to claim 13, further comprising:
    a carrier gas source connected to the connection cable.

17. The gas sensor device according to claim 16, wherein the carrier gas source comprises an inert gas source.

18. A method for the investigation of a geological formation, comprising the steps of:
    positioning a cylinder-shaped or tubular gas membrane sampling device in a geological formation, the gas membrane sampling device comprising
        a membrane element comprising a gas-permeable membrane that is liquid-tight relative to a liquid environment of the membrane element,
        a filler material comprising spheres of a solid inert materials, said filler material contained within and stabilizing the membrane element, and
        a connection cable being adapted for conducting gas out of the inner space of the membrane element through a bore hole to a surface location conducting gas out of the geological formation to a surface location, and
    analyzing the gas at the surface with an analyzing device.

19. The method according to claim 18, wherein the step of conducting the gas comprises:
    loading a carrier gas into the geological formation with a sample gas to be investigated using the membrane element of the gas membrane sampling device.

20. The method according to claim 19, wherein the carrier gas comprises an inert gas.

21. The method according to claim 19, wherein the sample gas comprises carbon dioxide.

22. The method according to claim 18, wherein the step of analyzing the gas comprises at least one of:
    mass-spectrometric analysis of the gas
    electro-chemical analysis, and
    gas-chromatographic analysis.

* * * * *